United States Patent [19]
Osborn, III

[11] Patent Number: 5,669,899
[45] Date of Patent: Sep. 23, 1997

[54] SANITARY NAPKIN WITH IMPROVED RELEASE LINER

[75] Inventor: Thomas W. Osborn, III, Cincinnati, Ohio

[73] Assignee: The Procter & Gamble Company, Cincinnati, Ohio

[21] Appl. No.: 679,039

[22] Filed: Jul. 12, 1996

[51] Int. Cl.$^6$ .................................................... A61F 13/15
[52] U.S. Cl. .................................................... 604/390; 604/387
[58] Field of Search ........................ 522/99; 604/387–390

[56] References Cited

U.S. PATENT DOCUMENTS

| | | | |
|---|---|---|---|
| 4,217,901 | 8/1980 | Bradstreet et al. | 604/387 |
| 4,629,643 | 12/1986 | Curro et al. | 428/131 |
| 5,436,281 | 7/1995 | Irifune et al. | 522/99 |

*Primary Examiner*—Robert A. Clarke
*Attorney, Agent, or Firm*—Kevin C. Johnson; Steven W. Miller; Jacobus C. Rasser

[57] ABSTRACT

A sanitary napkin having an improved release liner. The sanitary napkin includes a liquid pervious topsheet, a liquid impervious backsheet joined to the topsheet, and an absorbent core positioned between the topsheet and the backsheet. The backsheet has an inner surface and an outer surface. A pressure sensitive adhesive is positioned on the outer surface of the backsheet for securing the sanitary napkin in the crotch portion of a user's panty or undergarment. A release liner is releasably affixed to the adhesive in order to keep the adhesive from adhering to a surface other than the crotch portion of the panty prior to use. The release liner is a microapertured polymeric web.

16 Claims, 2 Drawing Sheets

SANITARY NAPKIN WITH IMPROVED RELEASE LINER

FIELD OF THE INVENTION

The present invention relates to a sanitary napkin, and more particularly, to a sanitary napkin having an improved release liner. As used herein, sanitary napkins are considered to be absorbent devices designed to be worn externally of the body by women, usually during their menstrual periods, to receive and contain menses and other vaginal discharges. Disposable sanitary napkins are intended to be discarded after use and soiling rather than being cleaned and reused.

BACKGROUND OF THE INVENTION

In their simplest form, disposable sanitary napkins comprise an absorbent element (sometimes referred to as an absorbent core) interposed between a pervious body-contacting element (sometimes referred to as a topsheet or an overwrap) and an impervious protective barrier (sometimes referred to as a backsheet). The absorbent element is, of course, intended to receive and contain menses and other vaginal discharges. The body-contacting element is intended to provide more or less dry-feeling contact with body surfaces while allowing free passage of fluids therethrough into the absorbent element. The protective barrier is intended to prevent menses or other vaginal discharges which escape from the absorbent element from soiling the user's garments.

In addition to the three functional elements mentioned above, disposable sanitary napkins are generally provided with means for attaching the device adjacent the user's crotch area, so that it remains in position as a user moves where it can most effectively perform its intended function. Typically, sanitary napkins are provided with an adhesive attachment means for securing the device to the inner crotch area of the user's undergarments.

Before the sanitary napkin is placed in use, the adhesive attachment means is typically covered with a removable release liner in order to keep the adhesive from adhering to a surface other than the crotch portion of the undergarment prior to use. Typical release liners comprise a substrate, such as paper, which has been coated with silicone. The silicone allows the release liner to be releasably secured to the adhesive thereby protecting the adhesive without diminishing the adhesive properties of the adhesive attachment means thus allowing the sanitary napkin to be secured to the user's undergarment once the silicone coated release liner has been removed.

While silicone coated release liners do perform their intended function, they tend to be somewhat expensive. Furthermore, these coated paper structures are noisy when removed from a sanitary napkin and when carded in a purse. Therefore, it would be desirable to provide a release liner providing all the benefits and functions of traditional silicone coated release liners but at a much lower cost. In addition, it would be desirable to provide a release liner providing all the benefits and functions of traditional silicone coated release liners but which are much quieter.

SUMMARY OF THE INVENTION

The present invention pertains to a sanitary napkin having an improved release liner. The sanitary napkin comprises a liquid pervious topsheet, a liquid impervious backsheet joined to the topsheet, and an absorbent core positioned between the topsheet and the backsheet. The backsheet has an inner surface and an outer surface. Adhesive attachment means, such as a pressure sensitive adhesive, is positioned on the outer surface of the backsheet for securing the sanitary napkin in the crotch portion of a user's panty or undergarment. A release liner is releasably affixed to the adhesive attachment means in order to keep the adhesive attachment means from adhering to a surface other than the crotch portion of the panty prior to use. The release liner comprises a microapertured polymeric web.

For the purpose of interpreting the present specification and claims, the term "macroscopically expanded", when used to describe three-dimensional plastic webs, ribbons and films of the present invention, refers to webs, ribbons and films which have been caused to conform to the surface of a three-dimensional forming structure so that both surfaces thereof exhibit a three-dimensional pattern of surface aberrations corresponding to the macroscopic cross-section of the forming structure, the surface aberrations comprising said pattern being individually discernible to the normal naked eye, i.e., a normal naked eye having 20/20 vision unaided by any instrument that changes the apparent size or distance of an object or otherwise alters the visual powers of the eye, when the perpendicular distance between the viewer's eye and the plan of the web is about 12 inches. Also, for the purpose of interpreting the present specification and claims, the term "planar", when utilized herein to describe plastic webs, ribbons and films of the present invention, refers to the overall condition of the web, ribbon or film when viewed by the normal naked eye on a macroscopic scale. In this context "planar" webs, ribbons and films may include webs, ribbons and films having a fine scale yet visible, pattern of surface aberrations on one or both sides thereof, the surface aberrations comprising said visible pattern not being individually discernible to the normal naked eye when the perpendicular distance between the viewer's eye and the plane of the web is about 12 inches.

BRIEF DESCRIPTION OF THE DRAWINGS

While the specification concludes with claims particularly pointing out and distinctly claiming the present invention, it is believed that the present invention will be better understood from the following description in conjunction with the following drawings in which like reference numbers identify identical elements and wherein:

DETAILED DESCRIPTION OF THE INVENTION

Figure 1:
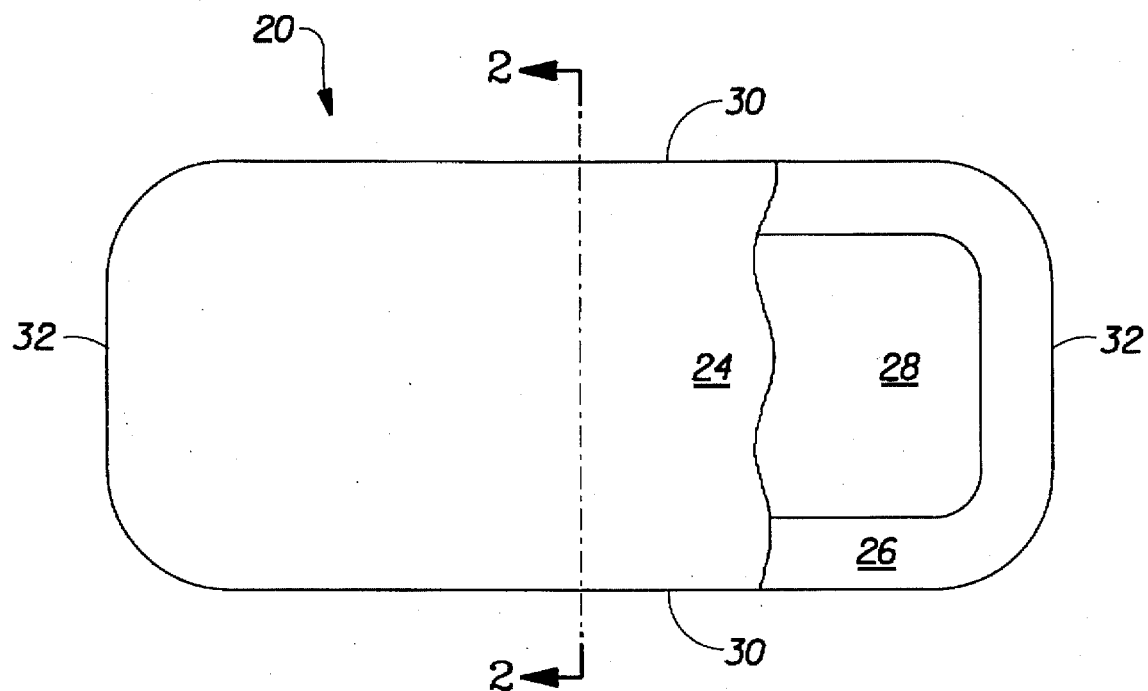
FIG. 1 is a top plan view of a sanitary napkin embodiment of the present invention having portions cut-away to reveal underlying structure.

FIG. 1 is plan view of the sanitary napkin 20 of the present invention in its flat-out state with portions of the structure being cut-away to more clearly show the construction of the sanitary napkin 20 and with the portion of the sanitary napkin 20 which faces or contacts the wearer, oriented towards the viewer. As shown in FIG. 1, sanitary napkin 20 preferably comprises a liquid pervious topsheet 24, a liquid impervious backsheet 26 joined with the topsheet 24, and an absorbent core 28 positioned between the topsheet 24 and the backsheet 26.

The sanitary napkin 20 has two surfaces, a body-contacting surface or "body surface" and a garment surface. The sanitary napkin 20 as shown in FIG. 1 is viewed from its body surface. The body surface is intended to be worn adjacent to the body of the wearer while the garment surface is on the opposite side and is intended to be placed adjacent the wearer's undergarments when the sanitary napkin 20 is worn. The sanitary napkin 20 has two centerlines, a longitudinal centerline and a transverse centerline. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction. FIG. 1 also shows that the sanitary napkin 20 has a periphery which is defined by the outer edges of the sanitary napkin 20 in which the longitudinal edges are designated 30 and the end edges are designated 32.

While the topsheet, the backsheet, and the absorbent core may be assembled in a variety of well known configurations (including so-called "tube" products or side flap products), preferred sanitary napkin configurations are described generally in U.S. Pat. No. 4,950,264, issued to Osborn on Aug. 21, 1990; U.S. Pat. No. 4,425,130, issued to DesMarais on Jan. 10, 1984; U.S. Pat. No. 4,321,924 issued to Ahr on Mar. 30, 1982; and U.S. Pat. No. 4,589,876, issued to Van Tilburg on Aug. 18, 1987. Each of these patents are hereby incorporated herein by reference.

FIG. 1 shows a preferred embodiment of the sanitary napkin 20 in which the topsheet 24 and the backsheet 26 have length and width dimensions generally larger than those of the absorbent core 28. The topsheet 24 and the backsheet 26 extend beyond the edges of the absorbent core 28 to thereby form portions of the periphery.

The absorbent core 28 may be any absorbent means which is capable of absorbing or retaining liquids (e.g., menses and/or urine). As shown in FIG. 1, the absorbent core 28 has a body surface, a garment surface, side edges, and pad edges. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures).

The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 26 and the topsheet 24 are positioned adjacent the garment surface and the body surface, respectively, of the absorbent core 28 and are preferably joined thereto and to each other by attachment means (not shown) such as those well known in the art. For example, the backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the sanitary napkin 20 such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 26 may permit vapors to escape from the absorbent core 28 (i.e., breathable) while still preventing exudates from passing through the backsheet 26.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. 4,950,254 issued to Osborn, incorporated herein by reference.

Figure 2:
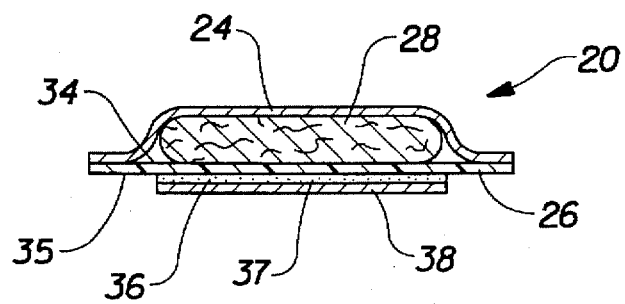
FIG. 2 is a cross-sectional view of the sanitary napkin shown in FIG. 1 taken along section line 2—2 of FIG. 1.

FIG. 2 is a cross-sectional view of the sanitary napkin 20 taken along section line 2—2 of FIG. 1. As can be seen in FIG. 2, the backsheet 26 has two surfaces, an inner surface 34 and an outer surface 35. The inner surface 34 is positioned adjacent the absorbent core 28 while the outer surface 35 is on the opposite side and is intended to be placed adjacent the wearer's undergarments when the sanitary napkin 20 is worn. The sanitary napkin 20 includes an adhesive attachment means 36 for attaching the sanitary napkin to the undergarment of the wearer. The adhesive attachment means 36 can he any conventional material such as adhesive 37 commonly used in the sanitary napkin art to secure sanitary napkins to the inner crotch area of the user's undergarments. Thus, a portion or all of the outer surface 35 of the hacksheet 26 is coated with an adhesive 37. Any adhesive or glue used in the art for such purposes can be used for the adhesive herein, with pressure-sensitive adhesive being preferred. Suitable adhesives are Fuller 2238 XZP and Fuller 1377 XZP manufactured by H. B. Fuller Company of St. Paul, Minnesota. Suitable adhesive fasteners are also described in U.S. Pat. No 4,917,697 issued to Osborn et al. on Apr. 17, 1990 and which is hereby incorporated herein by reference.

Figure 3:
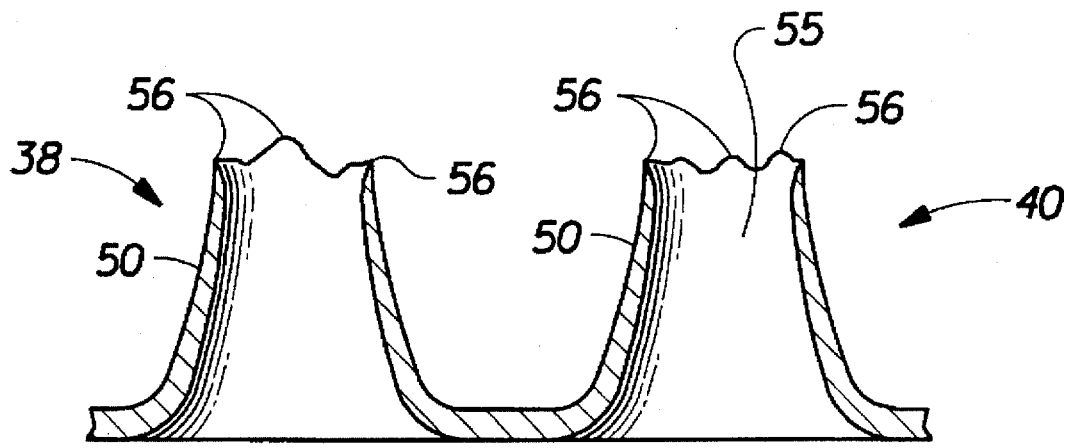
FIG. 3 is a greatly enlarged simplified schematic cross-sectional illustration of a planar polymeric web of the present invention having an overall fine scale pattern of surface aberrations each having a microaperture at the peak of each surface aberration.
Figure 4:
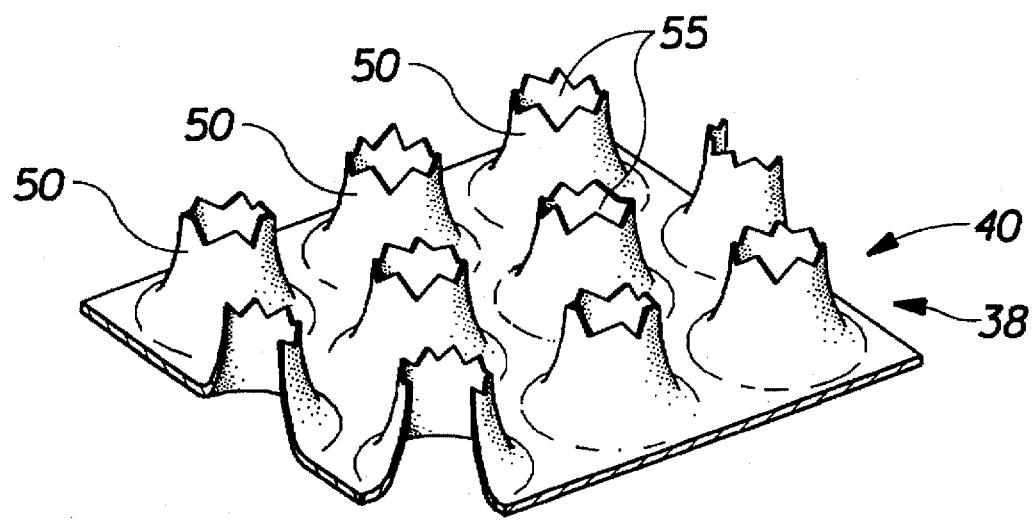
FIG. 4 is a greatly enlarged simplified perspective illustration of a segment of a microapertured web of the type generally illustrated in cross-section in FIG. 3.

Before the sanitary napkin 20 is placed in use, the adhesive attachment means 36 is covered with a removable release liner 38 in order to keep the adhesive from adhering to a surface other than the crotch portion of the panty prior to use. Referring to FIGS. 3 and 4 there is shown a particularly preferred embodiment of a release liner 38 of the present invention. The release liner 38 comprises a microapertured planar polymeric web 40. The microapertured polymeric web 40 exhibits a fine scale pattern of discrete surface aberrations 50. Each surface aberration 50 has its amplitude oriented substantially perpendicular to the surface in which the surface aberrations originates. At least one tiny aperture, i.e., a microaperture 55 is provided substantially coincidental with the maximum amplitude of each surface aberration. Each surface aberration 50 has a volcano-shaped aperture 55 having relatively thin, irregularly shaped petals 56 about its periphery. As can also be observed from FIG. 3, the outermost extremities of the petals 56 are substantially thinned. The microapertures 55 may be of any particular shape as desired.

It is important that the microapertures 55 be properly dimensioned such that they do not allow the passage of a significant amount of dirt or debris which could contaminate the adhesive. Preferably, the individual microapertured surface aberrations have a maximum cross-sectional dimension of about 20 mils or less, most preferably about 10 mils or less. The density of fine scale microapertured surface aberrations is at least about 400 aberrations per square inch, preferably at least about 1000 aberrations per square inch, more preferably at least about 2000 aberrations per square inch, and most preferably at least about 3000 aberrations per square inch. The density of fine scale microapertured surface aberrations may be as high as 10,000 aberrations per square inch. Further, it is preferred that the distance between any given microapertured surface aberration and an adjacent aberration in any given direction should not exceed about 25 mils, center-to-center. As can be seen in FIG. 3, the presence of the microapertures 55 significantly reduces the amount of polymeric material which comes into contact with the adhesive thus preserving the adhesive properties of the adhesive, while providing sufficient protection of the adhesive from din and other contaminants.

The microapertured web may be produced by impinging a jet of high pressure liquid on the exposed surface of a web of fiat polymeric film while the film is supported on a support member. An example of such a process is described in U.S. Pat. No. 4,629,643 issued to Curro et al. on Dec. 16, 1986 and is hereby incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary napkin comprising:
   a liquid pervious topsheet;
   a backsheet joined to said topsheet, said backsheet having an inner surface and an outer surface;
   an absorbent core positioned between said topsheet and said backsheet;
   adhesive attachment means located on the outer surface of said backsheet for securing said sanitary napkin to a user's panty; and
   a release liner releasably affixed to said adhesive attachment means, said release liner comprising an apertured polymeric web.

2. The sanitary napkin of claim 1 wherein said backsheet is liquid impervious.

3. The sanitary napkin of claim 1 wherein said adhesive attachment means comprises an adhesive.

4. The sanitary napkin of claim 1 wherein said apertured polymeric web comprises a microapertured polymeric web.

5. The sanitary napkin of claim 4 wherein said microapertured polymeric web exhibits a pattern of discrete surface aberrations each including at least one microaperture.

6. The sanitary napkin of claim 4 wherein said microapertured polymeric web comprises at least about 400 aberrations per square inch.

7. The sanitary napkin of claim 4 wherein said microapertured polymeric web comprises at least about 1000 aberrations per square inch.

8. The sanitary napkin of claim 4 wherein said microapertured polymeric web comprises at least about 2000 aberrations per square inch.

9. The sanitary napkin of claim 4 wherein said microapertured polymeric web comprises at least about 3000 aberrations per square inch.

10. A sanitary napkin comprising:
    a liquid pervious topsheet;
    a backsheet joined to said topsheet, said backsheet having an inner surface and an outer surface;
    an absorbent core positioned between said topsheet and said backsheet;
    adhesive attachment means located on the outer surface of said backsheet for securing said sanitary napkin to a user's panty; and
    a release liner releasably affixed to said adhesive attachment means, said release liner comprising a microapertured polymeric web exhibiting a pattern of discrete surface aberrations each including at least one microaperture.

11. The sanitary napkin of claim 10 wherein said backsheet is liquid impervious.

12. The sanitary napkin of claim 10 wherein said adhesive attachment means comprises an adhesive.

13. The sanitary napkin of claim 10 wherein said microapertured polymeric web comprises at least about 400 aberrations per square inch.

14. The sanitary napkin of claim 10 wherein said microapertured polymeric web comprises at least about 1000 aberrations per square inch.

15. The sanitary napkin of claim 10 wherein said microapertured polymeric web comprises at least about 2000 aberrations per square inch.

16. The sanitary napkin of claim 10 wherein said microapertured polymeric web comprises at least about 3000 aberrations per square inch.

* * * * *